US009629908B2

United States Patent
Benyacoub et al.

(10) Patent No.: US 9,629,908 B2
(45) Date of Patent: Apr. 25, 2017

(54) PROBIOTICS, SECRETORY IGA AND INFECTION

(71) Applicant: NESTEC S.A., Vevey (CH)

(72) Inventors: Jalil Benyacoub, Lausanne (CH);
Blaise Corthesy, Lausanne (CH);
Stephanie Blum-Sperisen, Pully (CH);
Laurent Favre, Puidoux-Gare (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 14/872,326

(22) Filed: Oct. 1, 2015

(65) Prior Publication Data
US 2016/0106834 A1    Apr. 21, 2016

Related U.S. Application Data

(63) Continuation of application No. 13/000,670, filed as application No. PCT/EP2009/057474 on Jun. 16, 2009, now Pat. No. 9,173,937.

(30) Foreign Application Priority Data

Jun. 24, 2008   (EP) .................................... 08158833

(51) Int. Cl.
*A61K 39/00*    (2006.01)
*A61K 39/235*    (2006.01)
(Continued)

(52) U.S. Cl.
CPC .......... *A61K 39/395* (2013.01); *A23L 33/135* (2016.08); *A23L 33/40* (2016.08);
(Continued)

(58) Field of Classification Search
CPC ...... A61K 35/74; A61K 35/744; A61K 39/00; A61K 2039/505
See application file for complete search history.

(56) References Cited

U.S. PATENT DOCUMENTS 5,531,988 A * 7/1996 Paul ...................... A23L 1/3056
424/130.1
2003/0074676 A1* 4/2003 Hodgkinson .......... A61K 35/20
800/7

(Continued)

FOREIGN PATENT DOCUMENTS

EP    0904784    *  3/1999    ............. A61K 35/74
EP    1661983       5/2006
(Continued)

OTHER PUBLICATIONS

International Scientific Association for Probiotics and Prebiotics "Clarification of the Definition of a Probiotic" Jun. 9, 2009, 2 pages.
(Continued)

*Primary Examiner* — Ja'Na Hines
(74) *Attorney, Agent, or Firm* — K&L Gates LLP (57) ABSTRACT

Ways to increase the effectiveness of probiotics is disclosed. One embodiment relates to a combination of probiotics with secretory IgA and possible uses of this combination. For example, a method of using a composition comprising secretory IgA and at least one probiotic to prepare a product to treat or prevent infection is disclosed.

14 Claims, 7 Drawing Sheets

(51) Int. Cl.
- A01N 63/00 (2006.01)
- A01N 65/00 (2009.01)
- A61K 39/395 (2006.01)
- A61K 35/744 (2015.01)
- A61K 35/745 (2015.01)
- A61K 35/747 (2015.01)
- A61K 35/741 (2015.01)
- A23L 33/00 (2016.01)
- A23L 33/135 (2016.01)

(52) U.S. Cl.
CPC .......... *A61K 35/741* (2013.01); *A61K 35/744* (2013.01); *A61K 35/745* (2013.01); *A61K 35/747* (2013.01); *A23V 2002/00* (2013.01)

(56) References Cited

U.S. PATENT DOCUMENTS

| | | | | |
|---|---|---|---|---|
| 2005/0079244 | A1* | 4/2005 | Giffard | A23C 9/206 426/42 |
| 2008/0145420 | A1* | 6/2008 | Simon | A61K 38/14 424/463 |
| 2011/0268743 | A1 | 11/2011 | Benyacoub et al. | |

FOREIGN PATENT DOCUMENTS

| | | | | |
|---|---|---|---|---|
| EP | 1854467 | 5/2011 | | |
| JP | 5589233 | 7/1980 | | |
| JP | 04342533 | 11/1992 | | |
| JP | 06234647 | 8/1994 | | |
| JP | 2011525483 | 9/2011 | | |
| WO | 9720577 | 6/1997 | | |
| WO | WO 2006/119560 | * 11/2006 | ............... | C07K 1/22 |
| WO | WO 2007/019901 | 2/2007 | | |

OTHER PUBLICATIONS

Iijima et al. "Mucosal immune network in the gut for the control of infectious diseases" Rev. Med. Virol., 2001, vol. 11, pp. 117-133.
Mathias et al. "Potentiation of Polarized Intestinal Caco-2 Cell Responsiveness to Probiotics Complexed with Secretory IgA" The Journal of Biological Chemistry, 2010, vol. 285, No. 44, pp. 33906-33913.
Europe Office Action for Application No. 09769156.2-1466, Dated Mar. 10, 2016, 11 pages.
Pant, N., et al., "Effective prophylaxis against rotavirus diarrhea using a combination of Lactobacillus rhamnosus GG and antibodies," BMC Microbiology, vol. 7, No. 86, Sep. 27, 2007, pp. 1-9, XP 021033260.
Phalipon, A., et al., "Novel functions for mucosal SIgA," Mucosal Immune Defence: Immunoglobulin A Springer, 2007, pp. 183-202, XP009107522.
Corthesy, B., et al., "Recombinant secretory immunoglobulin A in passive immunotherapy: Linking immunology and biotechnology," Current Pharmaceutical Biotechnology, vol. 4, No. 1, Feb. 1, 2003, pp. 51-67, XP009094155.
Corthesy, B., et al., "Secretory immunoglobulin A: From mucosal protection to vaccine development," Biological Chemistry, vol. 380, No. 11, Nov. 1999, pp. 1251-1262, XP009107514.
Pant, N., et al., "Lactobacilli expressing variable domain of Iliama heavy-chain antibody fragments (lactobodies) confer protection against rotavirus-induced diarrhea," Journal of Infectious Diseases, vol. 194, No. 11, Dec. 1, 2006, pp. 1580-1588, XP009107245.
Isolauri, E., et al., "Oral bacteriotherapy for viral gastroenteritis," Digestive Diseases and Sciences, vol. 39, No. 12, pp. 2595-2600.
Phalipon, A., et al., "Secretory Component: A New Role in Secretory IgA-Mediated Immune Exclusion in Vivo," Immunity, vol. 17, Jul. 2002, pp. 107-115.
Salminen, S., et al., "Probiotics: how should they be defined?" Trends in Food Science & Technology, vol. 10, 1999, pp. 107-110.
Gibson, G. et al., "Dietary Modulation of the Human Colonic Microbiota: Introducing the Concept of Prebiotics," Jounral of Nutrition. vol. 125, 1999, pp. 1401-1412.
Pant et al., (BMC Microbiology, pp. 1-9).
Kelly, Bovine Colostrums: A Review of Clinical Uses. Alternative Medicine Review. 2003. vol. 8(4):378-394).
International Search Report for International Application No. PCT/EP2009/057454 mailed on Sep. 14, 2009.
Written Opinion for International Application No. PCT/EP2009/057454 mailed on Sep. 14, 2009.
Araujo et al., (Acta Cir Bras. 2005;20 Suppl 1:178-84).
Annemiek et al., (Nutrition Research Reviews (1994), 7, 1-23).

* cited by examiner

PROBIOTICS, SECRETORY IGA AND INFECTION

PRIORITY CLAIM

The present application is a continuation of U.S. patent application Ser. No. 13/000,670, filed on Feb. 25, 2011, which is a National Stage of International Application No. PCT/EP09/057474, filed on Jun. 16, 2009, which claims priority to European Application No. 08158833.7, filed on Jun. 24, 2008, the entire contents of each of which are being incorporated herein by reference.

BACKGROUND

The present invention relates generally to the field of nutrition, health and wellness. In particular the present invention relates to probiotics and ways to increase their effectiveness. One embodiment of the present invention relates to a combination of probiotics with secretory IgA and possible uses of this combination.

An infection is the detrimental colonization of a host organism by foreign species. Usually, the infecting organism attempts to utilize the host's resources to promote its own multiplication. Thereby, the infecting organism, or pathogen, may interfere with the normal functioning of the host and can lead to more infection related disorders that may have a varying severity and that may lead in the worst case to death.

If there is a synergy between infecting organism and host, whereby the relationship is beneficial for the infecting organism but detrimental to the latter, is characterised as parasitism.

The list of disease linked to infection is huge and the costs associated with the treatment and prevention of infections are significant.

The market for antibacterial agents in the US alone is considered to be around 26 bn US-Dollars.

Infection can be treated today by proper medication. However, the selection of a proper medication requires defining the type of infection to be treated. Bacterial infections are often treated with antibacterial antibiotics. Taking the wrong antibacterial antibiotics in error for treating a specific non-viral infection won't treat the infection and may even be harmful. Further, such medication may always result in unwanted side effects and often requires the supervision of medical personnel.

Additionally, an extensive usage of antibiotics might contribute to the generation of antibiotic resistant infectious species. The Forbes Magazine states in June 2006 that drug resistant infections kill more Americans than AIDS and breast cancer combined.

Hence, the development of compositions that may contribute to reduce the need for antibiotics in society, is presently a key research focus.

Consequently, there is a need in the art for non-antibiotic compositions that can be administered, preferably on a day-to-day basis—without unwanted side effects and that can be used safely to treat or prevent infections, without the need to define the exact nature of the causative agent first.

One way to achieve this object is to administer a food composition comprising probiotics.

Probiotic micro-organisms are known to have a beneficial effect on the health and well-being of the host. In the last few decades, the use of probiotic bacteria has gained considerable attention as a safe and accessible form of treatment for example for gastrointestinal diseases (Isolauri E, et al., Dig Dis Sci 1994, 39:2595-2600). Typical probiotic bacteria that have been employed in this respect belong to the *Lactobacillus* or the *Bifidobacterium* genus.

The effectiveness of probiotics depends, in part, on their ability to resist to digestive tract conditions and adhere to intestinal epithelium. Moreover, a critical aspect conditioning their potential benefit to the host is the probiotic cross-talk with the host's environment and their impact on epithelium barrier and its function.

While some probiotics already achieve very respectable result in terms of colonization of the gastrointestinal tract, it would be desirable to have available a tool to further improve the effectiveness with which the probiotic micro-organisms colonize the gut.

SUMMARY

It was consequently the object of the present invention to provide the art with a composition that has the same advantages as the administration of probiotics to a subject in need thereof but that is even more effective in treating or preventing infections than the administration of probiotics alone.

The present inventors have addressed this need and found that they could achieve this object by a method and a food composition in accordance with the claims.

The present invention relates hence to a composition comprising antibodies, in particular secretory IgA, and at least one probiotic and to its use to treat, modulate, reduce and/or prevent infections.

Antibodies are often glycoproteins, which specifically recognise antigens. In vertebrates five immunoglobulin classes are described, including IgG, IgM, IgA, IgD and IgE, all of which differ in their function in the immune system. Secretory IgA (SIgA), which is the predominant and more stable immunoglobulin in intestinal mucosal secretions, was found to be in particular effective for the purpose of the present invention.

Without wishing to be bound by theory, the inventors believe that SIgA and probiotics may form complexes that may potentiate the interaction of probiotics with the host and improving their health benefit.

Figure 1:
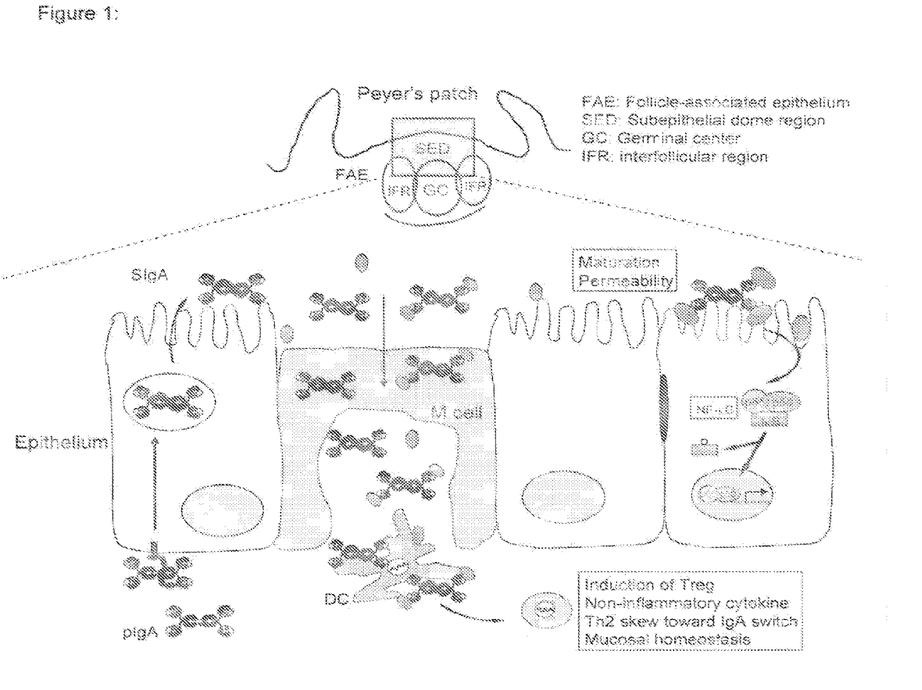
FIG. 1 shows schematically how SIgA is believed to improve the effects of commensal bacteria, when associated with them by increasing the interaction with the intestinal mucosa of the host.

The suggested mechanism of interaction of this combination with the intestinal mucosa of the host is presented in FIG. 1.

The first interaction of probiotics with the host occurs at the level of the gut mucosa. Among the key criteria for the selection of a probiotic micro-organism is its capacity to adhere to intestinal mucosa.

This adhesion seems to be required to block pathogen entry and to contribute to modulate protective immune functions, for example.

One of the most characteristic features of the mucosal immune system in most mammals is the dominant presence of secretory antibodies, particularly secretory IgA (SigA), an antibody class unique to mucosae.

Biosynthesis of polymeric IgA takes place in the mucosal lamina propria, and its transport across the epithelium lining the mucosal surfaces is ensured by the polymeric Ig receptor (pIgR) expressed by crypt and columnar epithelial cells.

In secretions, a significant portion of the pIgR termed the secretory component (SC) remains associated with polymeric IgA, releasing SIgA.

The release of SIgA into the lumen is dependent on the production of SC, whose expression is up-regulated after birth. pIgR appears to be critical to the stability and mucosal anchoring of the antibody (Phalipon et al. (2002) Secretory component: A new role in secretory IgA-mediated immune exclusion in vivo. Immunity 17:107-115).

Neonates, in which SIgA antibodies are barely detectable, depend on maternal IgG transferred through the placenta, and an exogenous supply of SIgA abundantly found in breast milk.

Together, this confers passive immunization in the gut essential to the protection of the host during the phase of shaping and maturation of the gastrointestinal immune system.

Hence the composition of the present invention will be in particular beneficial for newborns and infants (up to 2 years old), since they do not produce SIgA in sufficient amounts but rely on external supply.

The inventors presently believe that it is this association of SIgA with probiotics that potentiates the interaction of probiotics with the host, so that the resulting health benefits for the host are improved.

The present inventors have identified secretory IgA antibodies capable of associating with strains of commensal bacteria.

The present inventors have used in vitro Caco-2 epithelial cell monolayers to examine how SIgA favours the cross-talk between non-pathogenic bacteria and the epithelial surface. Two probiotic strains representative of the two main genders Lactobacilli and Bifidobacteria were evaluated as proof of principle, i.e. *Lactobacillus rhamnosus* NCC4007 (LPR) and *Bifidobacterium lactis* NCC2818 (BL818).

It was found that SIgA and/or SC, when associated with probiotics, promotes the interaction of probiotics with the host and modulates downstream processes involved in defense mechanisms.

This contributes to enhance the health benefits of probiotics. Through their combination with probiotics, SIgA and/or SC could optimally help trigger efficient protective host defense reactions, including responses against infections by various pathogens. Given their homeostatic effect, SIgA, combined with probiotics, will help to trigger an immune boosting effect against infections while preventing any potential damaging inflammatory process.

Consequently, one embodiment of the present invention is a composition comprising secretory IgA and at least one probiotic for the preparation of a product to treat or prevent non-viral infections.

The present invention also relates to the use of a composition comprising secretory IgA and at least one probiotic for the preparation of a product to treat or prevent non-viral infections.

The present invention additionally relates to a composition comprising SIgA and at least one probiotic for use in the treatment and/or prevention of non-viral infections.

The present invention extends to a composition comprising SIgA and at least one probiotic for treating and/or preventing non-viral infections.

The treatment of non-viral infections includes the reduction of non-viral infections.

"Probiotic" means microbial cell preparations or components of microbial cells with a beneficial effect on the health or well-being of the host. (Salminen S, Ouwehand A. Benno Y. et al "Probiotics: how should they be defined" Trends Food Sci. Technol. 1999:10 107-10).

All probiotic micro-organ isms may be used in accordance with the present invention. Preferably, they are selected from the group consisting of *Bifidobacterium, Lactobacillus, Streptococcus* and *Saccharomyces* or mixtures thereof, in particular selected from the group consisting of *Bifidobacterium longum, Bifidobacterium lactis, Lactobacillus acidophilus, Lactobacillus rhamnosus, Lactobacillus paracasei, Lactobacillus johnsonii, Lactobacillus plantarum, Lactobacillus salivarius, Enterococcus faecium, Saccharomyces boulardii* and *Lactobacillus reuteri* or mixtures thereof, preferably selected from the group consisting of *Lactobacillus johnsonii* (NCC533; CNCM I-1225), *Bifidobacterium longum* (NCC490; CNCM I-2170), *Bifidobacterium longum* (NCC2705; CNCM I-2618), *Bifidobacterium lactis* (2818; CNCM I-3446), *Lactobacillus paracasei* (NCC2461; CNCM I-2116), *Lactobacillus rhamnosus* GG (ATCC53103), *Lactobacillus rhamnosus* (NCC4007; CGMCC 1.3724), *Enterococcus faecium* SF 68 (NCIMB10415), and mixtures thereof.

The composition of the present invention may also contain prebiotics. The addition of prebiotics is beneficial as it can, when combined with probiotics delivers synergistic effects in terms of the health benefits. A composition comprising a combination of prebiotics and probiotics is commonly known as a symbiotic composition.

"Prebiotic" means food substances that promote the growth of probiotics in the intestines. They are not broken down in the stomach and/or upper intestine or absorbed in the GI tract of the person ingesting them, but they are fermented by the gastrointestinal microflora and/or by probiotics. Prebiotics are for example defined by Glenn R. Gibson and Marcel B. Roberfroid, Dietary Modulation of the Human Colonic Microbiota: Introducing the Concept of Prebiotics, J. Nutr. 1995 125: 1401-1412.

The prebiotics that may be used in accordance with the present inventions are not particularly limited and include all food substances that promote the growth of beneficial bacteria such as bifidobacteria or lactobacilli, and/or probiotics in the intestine. Preferably, they may be selected from the group consisting of oligosaccharides, optionally containing fructose, galactose, mannose; dietary fibers, in particular soluble fibers, soy fibers; inulin; or mixtures thereof. Preferred prebiotics are fructo-oligosaccharides (FOS), galacto-oligosaccharides (GOS), isomalto-oligosaccharides, xylo-oligosaccharides, oligosaccharides of soy, glycosylsucrose (GS), lactosucrose (LS), lactulose (LA), palatinose-oligosaccharides (PAO), malto-oligosaccharides, pectins and/or hydrolysates thereof.

The non-viral infection of the present invention may be a bacterial and/or a parasite infection. It may also be a fungal infection.

The non-viral infection may be a bacterial infection selected from an *Escherichia coli* infection, an *Vibrio cholerae* infection, a *salmonella* infection, a clostridia infection, a shigella infection, a parasite infection, including *Giardia lamblia, Entamoeba histolytica* and *Cryptosporidium* spp or mixtures thereof.

Typical bacterial infectious diseases that can be treated or prevented by the present invention include salmonellosis, shigellosis, typhoid fever, bacterial meningitis, anthrax, botulism, brucellosis, campylobacteriosis, cat scratch disease, cholera, diphtheria, epidemic typhus, gonorrhea, impetigo, legionellosis, leprosy (Hansen's Disease), leptospirosis, listeriosis, lyme disease, melioidosis, rheumatic fever, MRSA infection, nocardiosis, pertussis (whooping cough), plague, pneumococcal pneumonia, psittacosis, Q fever, Rocky Mountain Spotted Fever (RMSF), scarlet fever, syphilis, tetanus, trachoma, tuberculosis, tularaemia, typhus, and/or urinary tract infections Typical parasitic infectious diseases that can be treated or prevented by the present invention include african trypanosomiasis, amebiasis, ascariasis, babesiosis, Chagas disease, clonorchiasis, cryptosporidiosis, cysticercosis, diphyllobothriasis, dracunculiasis, echinococcosis, enterobiasis, fascioliasis, fasciolopsiasis, filariasis, free-living amebic infection, giardiasis, gnathostomiasis, hymenolepiasis, isosporiasis, kala-azar, leishmaniasis, malaria, metagonimiasis, myiasis, onchocerciasis, pediculosis, pinworm infection, scabies, schistosomiasis, taeniasis, toxocariasis, toxoplasmosis, trichinellosis, trichinosis, trichuriasis, trichomoniasis, and/or trypanosomiasis.

Typical fungal infectious diseases that can be treated or prevented by the present invention include aspergillosis, blastomycosis, candidiasis, coccidioidomycosis, cryptococcosis, histoplasmosis, and/or tinea pedis.

The product prepared by the use of the present invention may be a food product, an animal food product or a pharmaceutical composition. For example, the product may be a nutritional composition, a nutraceutical, a drink, a food additive or a medicament.

A food additive or a medicament may be in the form of tablets, capsules, pastilles or a liquid for example. Food additives or medicaments are preferably provided as sustained release formulations, allowing a constant supply of SIgA and probiotics for prolonged times.

The product is preferably selected from the group consisting of milk powder based products; instant drinks; ready-to-drink formulations; nutritional powders; nutritional liquids; milk-based products, in particular yoghurts or ice cream; cereal products; beverages; water; coffee; cappuccino; malt drinks; chocolate flavoured drinks; culinary products; soups; tablets; and/or syrups.

Milk may be any milk obtainable from animal or plant sources and is preferably cows milk, human milk, sheep milk, goat milk, horse milk, camel milk, rice milk or soy milk.

Instead of milk, also milk derived protein fractions or colostrum may be used.

The composition may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials. They may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. Further, they may contain an organic or inorganic carrier material suitable for oral or enteral administration as well as vitamins, minerals trace elements and other micronutrients in accordance with the recommendations of Government bodies such as the USRDA.

The composition of the present invention may contain a protein source, a carbohydrate source and/or a lipid source.

Any suitable dietary protein may be used, for example animal proteins (such as milk proteins, meat proteins and egg proteins); vegetable proteins (such as soy protein, wheat protein, rice protein, and pea protein); mixtures of free amino acids; or combinations thereof. Milk proteins such as casein and whey, and soy proteins are particularly preferred.

If the composition includes a fat source, the fat source more preferably provides 5% to 40% of the energy of the formula; for example 20% to 30% of the energy. DHA may be added. A suitable fat profile may be obtained using a blend of canola oil, corn oil and high-oleic acid sunflower oil.

A source of carbohydrates may more preferably provide between 40% to 80% of the energy of the composition. Any suitable carbohydrate may be used, for example sucrose, lactose, glucose, fructose, corn syrup solids, maltodextrins, and mixtures thereof.

The product prepared by the present invention may be administered to humans or animals, in particular companion animals, pets or livestock. It has beneficial effects for any age group. Preferably, the product is intended in for infants, juveniles, adults or elderly. It may however also be administered to mothers during pregnancy and lactation to treat the infant.

The composition of the present invention will be effective as long as probiotics and SIgA are administered simultaneously, briefly one after the other in a maximal timeframe of less than 60 minutes, preferably less than 30 minutes, more preferred less than 15 minutes and most preferred less than 5 minutes, and/or are combined prior to administration as already present in the food product.

However, it was found that the combination of probiotics and SIgA is in particular effective, if SIgA and probiotics are combined in complexes prior to administration. This has the advantage that the beneficial complexes do not need to form after consumption of the product, but that they are already present in the food product.

Consequently, one embodiment of the present invention relates to the use of a composition comprising SIgA and probiotics, wherein the SIgA molecule and at least one probiotic are at least partially associated in the composition.

SIgA and at least one probiotic are preferably present as immune complexes, for example in a way that at least 90%, more preferably at least 95%, even more preferred all probiotic bacteria are present as immune complex in association with at least 1 SIgA molecule, for example with at least 5 SIgA molecules.

The composition may also contain at least one other kind of other food grade bacteria, preferably selected from the group consisting of lactic acid bacteria, bifidobacteria, enterococci or mixtures thereof. These other food grade bacteria may contribute to obtain a healthy gut microflora and will hence contribute to achieve the object of the present invention even more effectively.

The present invention also relates to a food composition comprising SIgA and at least one probiotic micro-organism. The SIgA and the probiotic micro-organism may preferably be combined as a complex in the food composition. SIgA and the probiotic micro-organism may preferably be present in a stoichiometric ratio of at least 10:1, preferably at least 100:1, most preferably at least 2000:1 to 100000:1. The upper limit of SIgA saturation is determined by the surface of the probiotic micro-organisms and by the number of available binding sites for SIgA.

Typically, the probiotics will be effective in a large range amount. If the bacteria reach the intestine alive, a single bacterium can be sufficient to achieve a powerful effect by persisting in the gut and multiplication. However, in general, it is preferred if the product comprises between 102 and 1010 cells of probiotics per daily dose.

The amount of SIgA required to achieve an effect, is equally not limited. In principle one SIgA molecule combined with one probiotic micro-organism, preferably in the form of a complex, will be effective for the present invention. However, it is in generally preferred if the product comprises between 0.0001 mg secretory SIgA and 10 mg SIgA per daily dose.

Those skilled in the art will understand that they can freely combine all features of the present invention described herein, without departing from the scope of the invention as disclosed. In particular, features described for the uses of the present invention may be applied to the composition, e.g. the food composition, of the present invention and vice versa.

Further advantages and features of the present invention are apparent from the following Examples and Figures.

DETAILED DESCRIPTION

Example 1

Binding to Epithelial Cells

Approximately $10^6$ Caco-2 cells were seeded per 1 $cm^2$ Transwell filter. Cells were incubated for 16 h at 37° C. in absence of antibiotic or FCS with different doses of bacteria, as indicated in the figure legend. Fresh overnight cultures of LPR, BL818 and *E. coli* TG-1 bacteria were used. Cells were then washed prior to enumeration. Bound bacteria were counted by plating on MRS or LB plates. For each experiment, triplicate tests were performed. Data were expressed as means of bound bacteria per 100 Caco-2 cells±SEM. Triplicates were performed for each experiment. In a subsequent experiment, cells were incubated with $2 \times 10^7$ bacteria for 16 hours at 37° C., in the presence of increasing doses of either SIgA or SC as indicated in the legend to FIG. 3. Cells were then washed prior to enumeration. Bound bacteria were counted by plating on MRS or LB plates. For each experiment, triplicate tests were performed. Data were expressed as means of bound bacteria per 100 Caco-2 cells±SEM. Triplicates were performed for each experiment.

Figure 2:
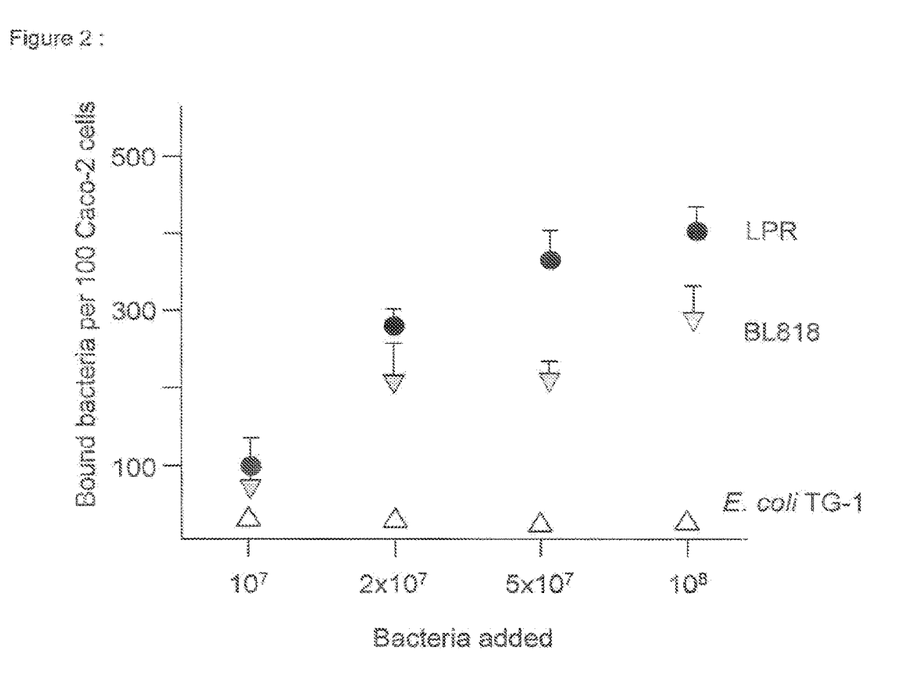
FIG. 2 shows the result of experiments testing the binding properties of two probiotic strains, *Lactobacillus rhamnosus* NCC4007 (LPR) and *Bifidobacterium lactis* NCC2818 (BL818), representative for the two main genders Lactobacilli and Bifidobacteria to epithelial cells. Data are expressed as means CFU per 100 Caco-2 cells±SEM.

A preferential binding to polarized Caco-2 cells of LPR or BL818 is observed in comparison to *E. coli* TG-1 (FIG. 2). There is a dose-dependent binding capacity of probiotics to intestinal epithelial cells. It can be observed that binding properties could be differentiated between the two strains.

For subsequent experiments, $2 \times 10^7$ CFU of probiotics were used, as this amount did not lead to any pH change in the medium on one hand, and showed an efficient binding ratio on the other hand.

Figure 3:
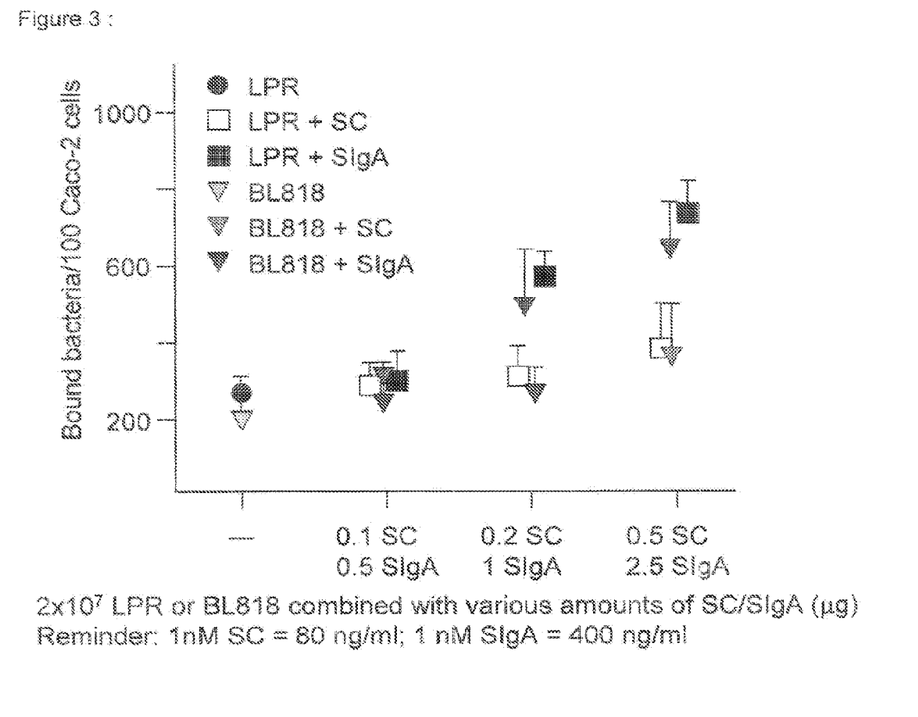
FIG. 3 shows the result of experiments testing the binding properties of two probiotic strains, *Lactobacillus rhamnosus* NCC4007 (LPR) and *Bifidobacterium lactis* NCC2818 (BL818), representative for the two main genders Lactobacilli and Bifidobacteria to epithelial cells and the influence of secretory IgA (SIgA) or secretory component (SC). Data are expressed as means CFU per 100 Caco-2 cells±SEM.

Increasing the dose of monoclonal SIgA potentiated the capacity of both LPR and BL818 to bind to polarized Caco-2 cell monolayers. When associated with the 20 bacteria, secretory component did not exhibit such properties (FIG. 3). The 1 μg dose of SIgA that confers a significant improvement in probiotic binding capacity was selected for subsequent experiments. This dose leads to the formation of a final complex constituted of approximately 50,000 to 100,000 units of SIgA for 1 bacterium.

Results are shown in FIGS. 2 and 3.

Example 2

Barrier Function in Polarized Caco-2 Cell Monolayer

Approximately $10^6$ Caco-2 cells were seeded per 1 $cm^2$ Transwell filter. Cells were incubated for 24 h at 37° C. with $2 \times 10^7$ CFU of bacteria in absence of antibiotic or FCS. Bacteria were tested either alone or in combination with SIgA or SC at concentrations indicated in the legend to FIG. 4. Transepithelial electrical resistance (TER) was measured at 3, 6, 9, 15 and 24 h. Controls include incubation with SIgA and SC alone. Triplicates were performed for each experiment.

Figure 4:
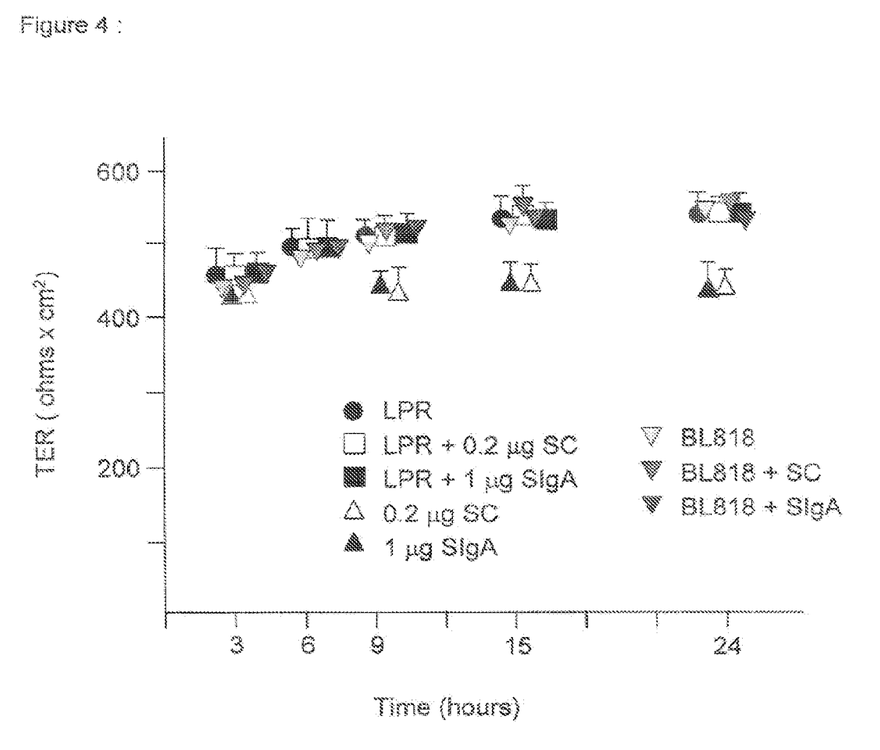
FIG. 4 shows the result of an experiment testing the effect of two probiotic strains, *Lactobacillus rhamnosus* NCC4007 (LPR) and *Bifidobacterium lactis* NCC2818 (BL818), representative for the two main genders Lactobacilli and Bifidobacteria, alone or in combination with SIgA or SC, on transepithelial electrical resistance (TER) measuring epithelial permeability. Data are expressed as means ohms per $cm^2 \pm SEM$.

A 20-25% increase in transepithelial electrical resistance (TER) resulted from the incubation of polarized Caco-2 cell monolayer with LPR or BL818 alone, suggesting that probiotics potentiated epithelial barrier function. This remained true when the bacteria were combined with SIgA or SC (FIG. 4). SIgA or SC by themselves did not lead to any TER change.

Results are shown in FIG. 4.

Example 3

NF-kB Activation in Polarized Caco-2 Cell Monolayer

Approximately $10^6$ Caco-2 cells were seeded per 1 $cm^2$ Transwell filter. Cells were incubated for 16 h at 37° C. with $2\times10^7$ CFU of LPR in absence of antibiotic or FCS. Bacteria were tested either alone or in combination with SIgA or SC at concentrations indicated in the legend to FIG. 5. $S.$ $flexneri$, $S.$ $typhi$ and $H.$ $pylori$ ($2\times10^7$ CFU) were used as pro-inflammatory pathogens in control experiments. Nuclear extracts were prepared and analysed by electrophoretic mobility shift assay (EMSA) to examine the binding of NF-κB to a specific DNA probe. Cytoplasmic extracts were obtained in parallel and the presence of IκBα was analyzed by Western blot using an anti-IκBα-specific monoclonal antibody to the protein.

Figure 5:
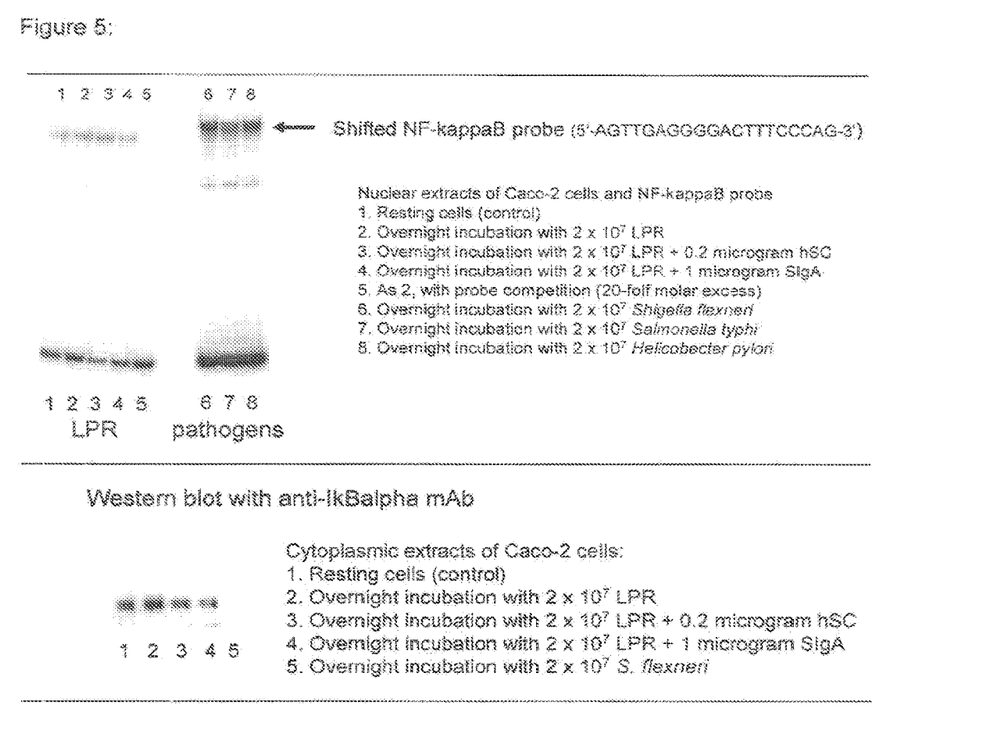
FIG. 5 shows the result of an experiment testing the effect of LPR, using SEQ. ID. NO. 1 as the shifted NF-kappaB probe, combined or not with SIgA or SC, on NF-KB activation in Caco-2 cell monolayer. Decrease in NF-KB binding activity is indicative of attenuated inflammatory pathway(s) within the Caco-2 cell.

Exposure of polarized Caco-2 cell monolayers to pathogenic bacteria led to a much more pronounced activation of nuclear NF-κB compared to non-pathogenic bacteria (FIG. 5).

Disappearance of IκBα (lower panel) reflects activation of the pathway leading to nuclear translocation of NF-κB. In that respect, while LPR alone has a mild effect on NF-$_k$B activation, combination of LPR with SIgA or SC reduced NF-κB activation in Caco-2 cells (BL818 not tested). As expected, incubation of epithelial cells with pathogenic $S.$ $flexneri$ led to a complete disappearance of IκBα expression.

Results are shown in FIG. 5.

Example 4

Anti-Pathogenic Activity

Approximately $10^6$ Caco-2 cells were seeded per 1 $cm^2$ Transwell filter. Cells were incubated for 16 h at 37° C. with $2\times10^7$ CFU of LPR in absence of antibiotic or FCS. LPR was tested alone or in combination with with either 0.2 µg of SC, 1 µg of polyclonal SIgA or 1 g of specific anti-$S.$ $flexneri$ LPS SIgAC5. After incubation with LPR cells were washed and then incubated with $10^7$ $S.$ $Flexneri$ for 6 hours, washed again and incubated with 50 g/ml gentamycin for 45 min. Finally, cells were lysed and intracellular $S.$ $flexneri$ were enumerated on LB agar plates. Triplicates were performed for each experiment.

Addition of LPR reduced infection of polarized Caco-2 cell monolayer by $S.$ $flexneri$ in a dose dependent manner. The effect was highly enhanced upon combination with SIgA. Full prevention of infection was achieved when $S.$ $flexneri$ LPS-specific SIgAC5 antibody was used (FIG. 6).

Figure 6:
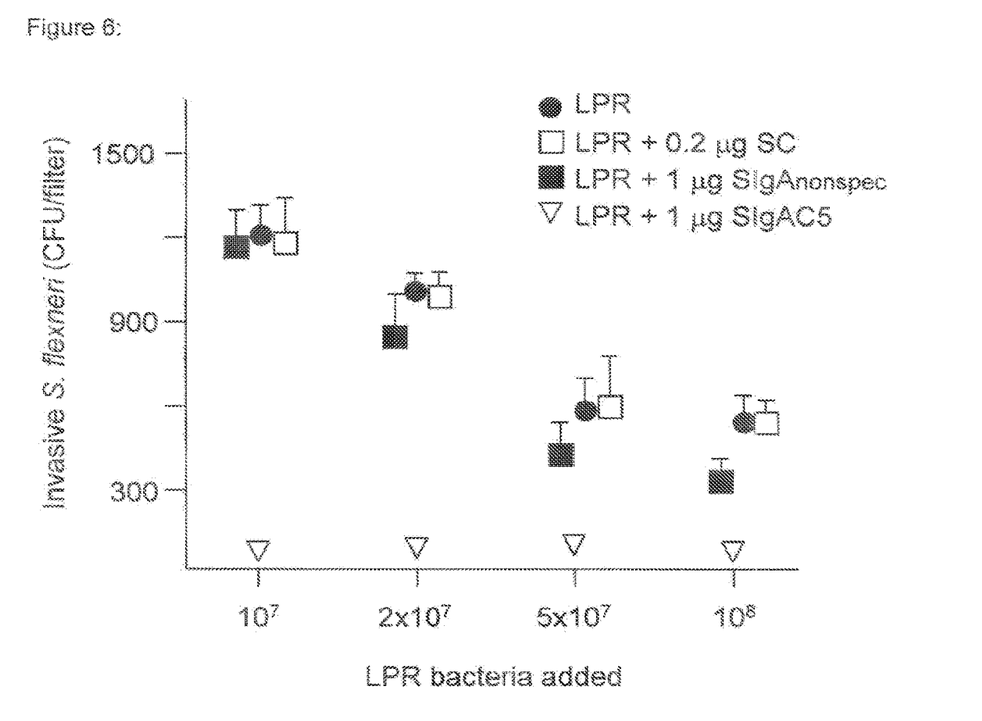
FIG. 6 shows the result of an experiment testing the effect of LPR, combined or not with SIgA or SC, on *S. flexneri* invasion of Caco-2 cell. Two monoclonal SigA molecules were used: a non-specific SIgA (SlgAnon-spec) recognizing a *Salmonella* epitope, and the specific anti-*S. flexneri* SIgAC5. Data are expressed as means CFU per Transwell filter±SEM.

Results are shown in FIG. 6.

Example 5

Expression of Polymeric Ig Receptor in Polarized Caco-2 Cell Monolayer

Approximately $10^6$ Caco-2 cells were seeded per 1 $cm^2$ Transwell filter. Cells were incubated for 16 h at 37° C. with $2\times10^7$ CFU of LPR or BL818 in absence of antibiotic or FCS. Probiotics were tested alone or in combination with with either 0.2 µg of SC or 1 µg of polyclonal SIgA. Control $S.$ $flexneri$ was tested alone or in combination with 1 µg of specific anti-$S.$ $flexneri$ LPS SIgAC5. After washing, Caco-2 cells were directly recovered from the Transwell filters and lysed. Nuclei were removed and cell debris as well as cytoplasms were analyzed by Western blot using anti-pIgR antibody and antisera to human SC and β-actin as controls. Triplicates were performed for each experiment.

Figure 7:
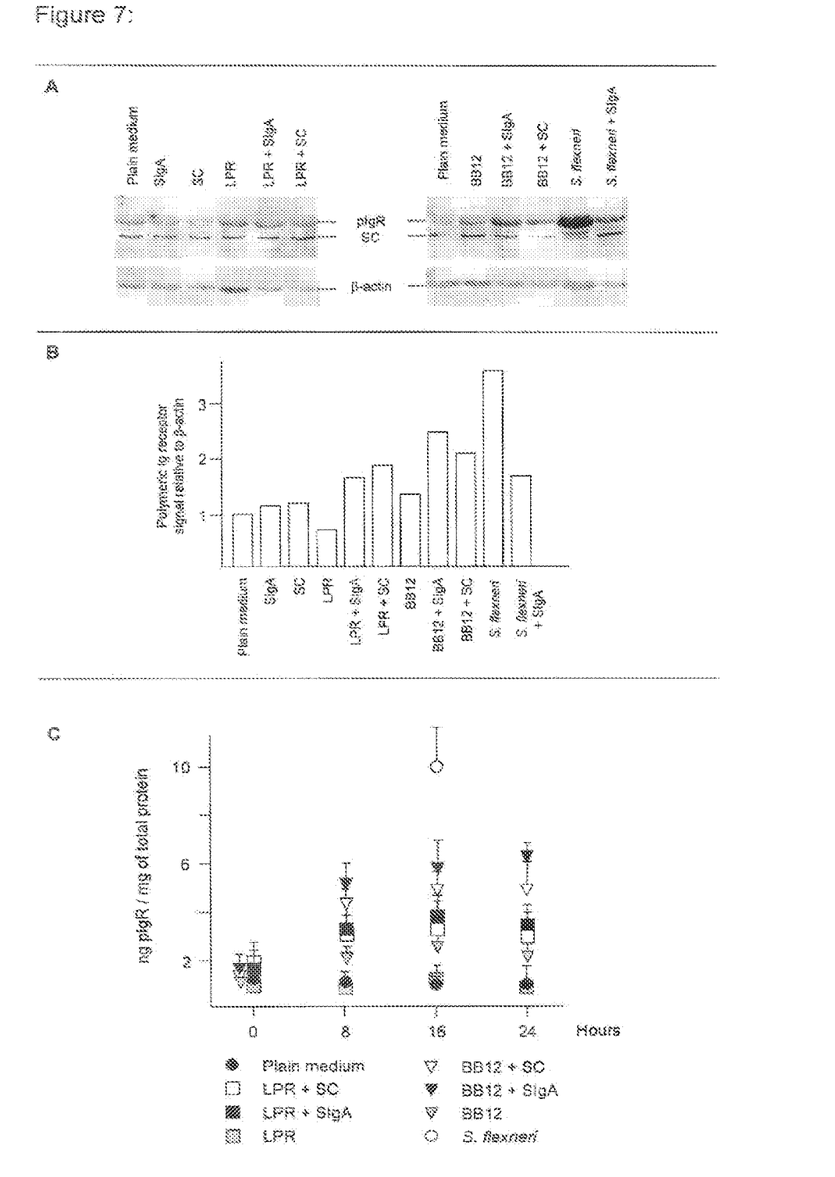
FIG. 7 shows the result of an experiment testing the effect of probiotics on polymeric Ig receptor (pIgR) expression in a Caco-2 monolayer. Different treatments tested at 16 h, including combination of probiotics with non-specific SIgA and combination of *S. flexeneri* with specific anti-*S. flexneri* SIgA. (A) Different treatments tested at 16 h, including combination of probiotics with non-specific SIgA and combination of *S. flexneri* with specific anti-*S. flexneri* SIgA. The presence of pIgR was assessed by western blot, as was β-actin. (B) Semi-quantitative analysis of pIgR expression levels normalized to β-actin by densitometric analysis of the bands identified in the gels in A. (C) Kinetics of pIgR expression over 24 h incubation of Caco-2 cells with various preparations, as measured by ELISA.

In a subsequent experiment cells were incubated following the same procedure and then recovered from the Transwell filter after 8, 16 and 24 h of incubation. Quantitative analysis of pIgR was performed by ELISA on cell debris/cytoplasms fractions. Total proteins were determined by the BCA protein assay. Values were normalized to protein content and data expressed as means of ng pIgR/mg of total protein±SEM.

pIgR expression in epithelial cells was normalized to β-actin expression. As revealed by Western blot (upper panel) and densitometric analysis of the respective signals (lower panel), there was an increase of pIgR level following overnight exposure of polarized Caco-2 monolayers to combinations of LPR or BL818 with either SIgA or SC compared to probiotics alone (FIG. 7a). Specific anti-$S.$ $flexneri$ LPS SIgAC5 prevented interaction of the pathogen with the Caco-2 cell polarized monolayer, thus explaining the decrease in pIgR expression when compared to $S.$ $flexneri$ treatment alone.

The results further showed a time-dependent increase of polymeric Ig receptor (pIgR) level following exposure of polarized Caco-2 cell monolayers to probiotic combinations with SIgA or SC (FIG. 7b).

Results are shown in FIG. 7.

The invention is claimed as follows:

1. A product comprising SIgA and a probiotic micro-organism and selected from the group consisting of a food product formulated for consumption by humans, an animal food product, and a pharmaceutical composition, the SIgA and the probiotic micro-organism are present in the form of a complex with each other, and the SIgA and the probiotic micro-organism are present in the product in a stoichiometric ratio of at least 100:1.

2. The product of claim 1 wherein the product is formulated for administration to at least one individual selected from the group consisting of a newborn, an infant, a juvenile, an adult, an elderly individual, and a mother during pregnancy or lactation.

3. The product of claim 1 comprising milk from an animal or plant source.

4. The product of claim 3 wherein the milk is selected from the group consisting of cow milk, human milk, sheep milk, goat milk, horse milk, camel milk, rice milk and soy milk.

5. The product of claim 1 comprising milk-derived protein fractions or colostrum.

6. The product of claim 1 comprising a prebiotic.

7. The product of claim 6 wherein the prebiotic is selected from the group consisting of oligosaccharides, dietary fibers, and mixtures thereof.

8. The product of claim 6 wherein the prebiotic is selected from the group consisting of fructo-oligosaccharide, galacto-oligosaccharide, manno-oligosaccharide, soluble fiber, soy fiber, inulin, and mixtures thereof.

9. The product of claim 6 wherein the prebiotic is selected from the group consisting of fructo-oligosaccharide, galacto-oligosaccharide, isomalto-oligosaccharide, xylooligosaccharide, an oligosaccharide of soy, glycosyl sucrose, lactosucrose, lactulose, palatinoseoligosaccharide, maltooligosaccharide, pectin, hydrolysates thereof, and mixtures thereof.

10. The product of claim 1 comprising between $10^2$ and $10^{10}$ cells of the probiotic micro-organism per daily dose.

11. The product of claim 1 comprising between 0.0001 mg and 10 mg of the SIgA per daily dose.

12. The product of claim 1 wherein the probiotic micro-organism is selected from *Bifidobacterium, Lactobacillus, Streptococcus, Saccharomyces* and mixtures thereof.

13. The product of claim 1 wherein the probiotic micro-organism is selected from the group consisting of *Bifidobacterium longum, Bifidobacterium lactis, Lactobacillus acidophilus, Lactobacillus rhamnosus, Lactobacillus paracasei, Lactobacillus johnsonii, Lactobacillus plantarum, Lactobacillus salivarius, Enterococcus faecium, Saccharomyces boulardii, Lactobacillus reuteri*, and mixtures thereof.

14. The product of claim 1 wherein the probiotic micro-organism is selected from the group consisting of: *Lactobacillus johnsonii* NCC533 (CNCM I-1225), *Bifidobacterium longum* NCC490 (CNCM I-2170), *Bifidobacterium longum* NCC2705 (CNCM I-2618), *Bifidobacterium lactis* NCC2818 (CNCM I-3446), *Lactobacillus paracasei* NCC2461 (CNCM I-2116), *Lactobacillus rhamnosus* GG (ATCC53103), *Lactobacillus rhamnosus* NCC4007 (CGMCC 1.3724), *Enterococcus faecium* SF 68 (NCIMB10415), and mixtures thereof.

\* \* \* \* \*

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Synthesized: Shifted NF-kappaB Probe Sequence

<400> SEQUENCE: 1
agttgagggg actttcccag                                               20
```